United States Patent
Ogura et al.

(10) Patent No.: US 11,191,523 B2
(45) Date of Patent: Dec. 7, 2021

(54) ULTRASONIC IMAGE CONSTRUCTION METHOD, ULTRASONIC IMAGE CONSTRUCTION APPARATUS, ULTRASONIC IMAGE CONSTRUCTION PROGRAM, AND SKIN EVALUATION METHOD

(71) Applicants: HONDA ELECTRONICS CO., LTD., Aichi (JP); NATIONAL UNIVERSITY CORPORATION TOYOHASHI UNIVERSITY OF TECHNOLOGY, Aichi (JP); SHISEIDO COMPANY, LTD., Tokyo (JP)

(72) Inventors: Yuki Ogura, Kanagawa (JP); Naohiro Hozumi, Aichi (JP); Sachiko Yoshida, Aichi (JP); Kazuto Kobayashi, Aichi (JP)

(73) Assignees: HONDA ELECTRONICS CO., LTD., Aichi (JP); NATIONAL UNIVERSITY CORPORATION TOYOHASHI UNIVERSITY OF TECHNOLOGY, Aichi (JP); SHISEIDO COMPANY, LTD., Tokyo (JP)

(*) Notice: Subject to any disclaimer, the term of this patent is extended or adjusted under 35 U.S.C. 154(b) by 0 days.

(21) Appl. No.: 16/611,498

(22) PCT Filed: May 10, 2017

(86) PCT No.: PCT/JP2017/017651
§ 371 (c)(1),
(2) Date: Nov. 7, 2019

(87) PCT Pub. No.: WO2018/207276
PCT Pub. Date: Nov. 15, 2018

(65) Prior Publication Data
US 2020/0375573 A1    Dec. 3, 2020

(51) Int. Cl.
*A61B 8/14* (2006.01)
*A61B 8/08* (2006.01)
(Continued)

(52) U.S. Cl.
CPC .......... *A61B 8/5207* (2013.01); *A61B 8/0858* (2013.01); *A61B 8/14* (2013.01);
(Continued)

(58) Field of Classification Search
CPC ....... A61B 8/0858; A61B 18/02; A61B 18/06; A61B 18/082; A61B 18/1492;
(Continued)

(56) References Cited

U.S. PATENT DOCUMENTS 6,494,097 B1    12/2002  Shihadeh
2008/0194952 A1*  8/2008  Luo ..................... A61B 8/0875
                                                        600/437

FOREIGN PATENT DOCUMENTS

JP    2006-271765    10/2006

OTHER PUBLICATIONS

C.M.W. Daft et al., "Frequency dependence of tissue attenuation measured by acoustic microscopy", J. Acoust. Soc. Am., May 1989, p. 2194-2201.

* cited by examiner

*Primary Examiner* — Mark D Remaly
(74) *Attorney, Agent, or Firm* — Clark & Brody LP

(57) ABSTRACT

An ultrasonic-image-construction apparatus can construct an ultrasonic-tomographic image of a thin, layer-structured target object to be measured relatively easily and highly accurately in a manner in which such layered structure is easily understood. An ultrasonic transducer of an ultrasonic-image-constructing apparatus transmits ultrasonic waves to the target object. A reference substance makes contact with
(Continued)

a base substrate, with such ultrasonic waves being incident on the target object via the base substrate, then receives an impulse response of an ultrasonic waveform. A computing means performs calculation to estimate acoustic-physical-property distribution in consideration of the multiple-reflections influence based on normalized-impulse information obtained from impulse-response information of such ultrasonic waveform incident on the reference substance and from impulse-response information of such ultrasonic waveform incident on the target object. The image-construction means constructs acoustic-physical-property-image data based on acoustic-physical-property distribution in the depth direction obtained by computing means.

11 Claims, 11 Drawing Sheets

(51) Int. Cl.
*G01B 15/02* (2006.01)
*G01N 29/44* (2006.01)

(52) U.S. Cl.
CPC .......... *G01B 15/02* (2013.01); *G01N 29/4436* (2013.01); *G01N 2291/02475* (2013.01)

(58) Field of Classification Search
CPC .......... A61B 2017/00026; A61B 2017/00084; A61B 2017/00106; A61B 2018/0022; A61B 2018/00303; A61B 2018/00327; A61B 2018/00577; A61B 2018/00642; A61B 2018/0088; A61B 2018/00904; A61B 2018/0212; A61B 2018/0262; A61B 2034/2051; A61B 2034/2063; A61B 2090/061; A61B 2090/064; A61B 2090/3784; A61B 34/20; A61B 34/76; A61B 8/06; A61B 8/085; A61B 8/12; A61B 8/4466; A61B 8/4477; A61B 8/461; A61B 8/463; A61B 8/485
See application file for complete search history.

Subjects in their 20's

Subjects in their 40's

Subjects in their 60's

ULTRASONIC IMAGE CONSTRUCTION METHOD, ULTRASONIC IMAGE CONSTRUCTION APPARATUS, ULTRASONIC IMAGE CONSTRUCTION PROGRAM, AND SKIN EVALUATION METHOD

TECHNICAL FIELD

This invention relates to a method and to an apparatus for constructing an image of living tissue or the like based on information obtained by using ultrasonic waves, and it relates to a program therefor and to a skin-evaluation method.

TECHNICAL BACKGROUND

Evaluation of the dynamic properties of the surface and inside of an object is useful in various fields. For example, in the case of a biological body, tissue fibrosis that occurs in a lesion such as cancer is known as a phenomenon of which the tissue is hardened compared to the surrounding area of such tissue. Since dynamic characteristics are linked with acoustic characteristics, if the value of the acoustic characteristic value within a biological body changes due to hardening of the surrounding tissue, the reflection of ultrasonic waves also changes accordingly. By knowing this phenomenon, attempts have been made to detect changes in dynamic properties within a biological body from changes in the brightness of a B-mode echo image. In addition to inferring changes in dynamic properties from a B-mode echo image, various measuring techniques e.g. using ultrasonic elastography to capture the transmission of shear waves in a B-mode echo image in applying acoustic-radiation pressure, thus detecting through the movement of such shear waves that changes in the dynamic properties within such a biological body have been developed. From these facts, it is recognized now that the evaluation of internal dynamic properties is significant in the medical field or the like.

The use of an ultrasonic B-mode echo image is a method widely used in the medical field, and many apparatuses for obtaining such an image have been proposed (see Patent Document 1). Briefly, an ultrasonic B-mode echo image is an image of a reflected signal sequence of which an ultrasonic wave incident on an object is reflected and returned. When it is assumed that the ultrasonic waves have traveled straight without having scattered, a reflection occurs due to the difference in the resistance value (acoustic impedance) at the travel destination, the same as in the case of an electrical signal. Therefore, if the distribution of acoustic impedance is known, it is possible to estimate what kind of reflected signal-sequence has returned. In other words, if the distribution of the acoustic property is known, it is possible to estimate that which the B-mode image is supposed to have observed and vice versa.

PRIOR ARTS

Patent Document

Patent Document 1: Japanese Published Unexamined Application No. 2006-271765

DISCLOSURE OF THE INVENTION

Problems to be Solved by the Invention

However, as for target objects of non-uniform thickness (depth) such as biological tissue or the like, the reflected waveform that penetrates and returns from such tissue reflects the result of ultrasonic-waves incident on the target object having undergone enormous scattering and absorption in various ways of traveling (the result of multiple reflection). For this reason, it is considered difficult to convert such a reflected waveform into acoustic properties such as an acoustic impedance or the like, and this method has not been studied in the past. Also, since an ultrasonic B-mode echo image tends to be an image disturbed by speckle noise caused by multiple reflections of ultrasonic waves within a biological tissue, it is considered unsuitable for displaying the internal structure of such biological tissue with a high degree of accuracy. Therefore, of the conventional apparatus, a countermeasure such as an acoustic filter is required, and there is a problem that the configuration is complicated.

Furthermore, regarding a normal ultrasonic-diagnostic apparatus that displays an ultrasonic B-mode echo image, at least information about the layered structure within a biological tissue such as skin or the like can be obtained. However, the obtained image is a reflected image of the interface between such structured layers of different acoustic impedances, and such a reflected image is insufficient to perceive the internal structure of such biological tissue. Specifically, it is insufficient to perceive the difference in acoustic impedance within such biological tissue. In other words, it was easy to sensuously understand the reflected image obtained by the prior art whereof the interface of such layered structure existed. On the other hand, it was difficult to understand sensuously how the acoustic impedance of the intermediate region surrounded by such interface existed. Therefore, it has been desirable to construct an ultrasonic-tomographic image of a very thin target object to be measured having a layered structure in a fashion that makes it sensuously easy to understand such layered structure based on the information obtained by using ultrasonic waves.

This invention was achieved in light of the above problems, and one of its objectives was to provide an ultrasound image-construction method, an ultrasound image-construction apparatus and an ultrasound image-construction program that can construct an ultrasonic-tomographic image of a very thin target object to be measured having a layered structure in a mode that makes it sensuously easy to understand such layered structure in a relatively simple way with a high degree of accuracy.

Another objective is to provide a method capable of simply and non-invasively evaluating a skin condition based on information obtained using ultrasonic waves.

Means for Solving the Problems

As described above, it is considered difficult to convert a reflected waveform from a target object to be measured into acoustic properties, thus such a measuring method has not been studied in the past. The inventors of this invention dared to convert the reflected-signal sequence that is the basis of an ultrasonic B-mode image into an acoustic-physical property (dynamic-physical property), thus conceiving the construction of an acoustic physical-property image. Then, after extensive study was done by the inventors of this invention to solve the above problems, the inventors obtained "standardized impulse-response information," that is apparatus independent impulse-response information from the impulse-response information of the ultrasonic-waveform incident on the reference substance and from the impulse-response information of the ultrasonic-waveform incident on the target object to be measured. As such, the inventors finally learned that it is possible to estimate accurately the acoustic-property distribution in the depth direction by using such information. Also, in estimating the acoustic-property distribution, they learned that it is possible to estimate accurately the acoustic-property distribution in the depth direction by performing a calculation, in consideration of the effect of multiple reflections, by using a method that can eliminate such an effect. The inventors of this invention, on the basis of these findings, have earnestly studied further and have thought of the means for solving the problems as listed below.

(1) An ultrasonic-image-construction method, characterized in comprising a transmitting-and-receiving step for transmitting ultrasonic waves in a state thereof that a target object to be measured and a reference substance of known acoustic properties are in contact with a base substrate of known acoustic properties, and then such step for receiving the impulse responses of such ultrasonic waveform from the target object to be measured and from the reference substance, with such ultrasonic waves being incident on the target object to be measured and on the reference substance through the base substrate; and in comprising a computing step for performing a calculation to estimate the acoustic-property distribution in the depth direction in consideration of the effect of multiple reflections based on the normalized impulse-response information having been obtained from the impulse-response information of the ultrasonic waveform incident on the reference substance and of the impulse-response information of the ultrasonic waveform incident on the target object to be measured; and in comprising an image-construction step for constructing the acoustic-property image data having been obtained based on the acoustic-property distribution in the depth direction obtained by the computing means.

(2) An ultrasonic image-construction method according to means (1), characterized in that the target object to be measured is biological tissue.

(3) An ultrasonic image-construction method according to means (1), characterized in that the target object to be measured is skin.

(4) An ultrasonic-image-construction method according to any one of means (1) to (3), characterized in that the base substrate is at least partially flat and is made of a material harder than the target object to be measured.

(5) An ultrasonic-image-construction method according to any one of means (1) to (4), characterized in that the reference substance of known acoustic properties that is different from the base substrate is already provided on the surface of the base substrate on which the target object to be measured is arranged.

(6) An ultrasonic-image-construction method according to any one of means (1) to (5), characterized in that in the transmitting-receiving step an ultrasonic wave is incident on the target object to be measured while such ultrasonic wave is relatively scanning in a one-dimensional or two-dimensional direction.

(7) An ultrasonic-image-construction method according to any one of means (1) to (6), characterized in that in assuming that in the calculation step the lossless microtransmission paths of different acoustic impedances are connected in the depth direction to form an assembly of transmission paths, a calculation to estimate the acoustic-impedance distribution in the depth direction of the transmission path is done by sequentially repeating the process of estimating the acoustic impedance of the micro-transmission path adjacent to the back side based on the estimated result of the acoustic impedance of the microtransmission path on the front side.

(8) An ultrasonic-image-construction apparatus, characterized in comprising an ultrasonic transducer that transmits ultrasonic waves in a state thereof that a target object to be measured and a reference substance of known acoustic properties are in contact with a base substrate of known acoustic properties, and of which such ultrasonic transducer receives the impulse responses of ultrasonic waveforms from the target object to be measured and from the reference substance, with such ultrasonic waves being incident on the target object to be measured and on the reference substance through the base substrate, and in comprising a computing means for estimating the acoustic-property distribution in the depth direction in consideration of the effect of multiple reflections based on the impulse-response information of the ultrasonic waveform having been incident on the reference substance and based on the normalized impulse-response information having been obtained from the impulse-response information of the ultrasonic waveform having been incident on the target object to be measured; and in comprising an image-construction means for constructing the acoustic-property image data having been obtained based on the acoustic-property distribution in the depth direction obtained by the computing means.

(9) An ultrasonic-image-construction apparatus according to means (8), characterized in further comprising a scanning means for relatively scanning the ultrasonic transducer to the target object to be measured in a one-dimensional or two-dimensional direction.

(10) An ultrasonic-image-construction program to run a processor; to execute a transmitting-and-receiving step for transmitting ultrasonic waves in a state thereof that a target object to be measured and a reference substance of known acoustic properties are in contact with a base substrate of known acoustic properties, and then such step for receiving the impulse responses of such ultrasonic waveform from the target object to be measured and from the reference substance, with such ultrasonic waves being incident on the target object to be measured and on the reference substance through the base substrate; to execute a calculating step for performing a calculation to estimate the acoustic-property distribution in the depth direction in consideration of the effect of multiple reflections based on the normalized impulse-response information having been obtained from the impulse-response information of the ultrasonic waveform incident on the reference substance and of the impulse-response information of the ultrasonic waveform incident on the target object to be measured; and to execute an image construction step for constructing the acoustic-property image data having been obtained based on the acoustic-property distribution in the depth direction obtained by the computing means.

(11) A skin-evaluation method, characterized in comprising a transmitting and receiving step for transmitting ultrasonic waves to the ultrasonic transducer in a state thereof the target object to be measured and the reference substance of known acoustic properties are placed in contact with the base substrate of known acoustic properties, and then such step for receiving the impulse responses of the ultrasonic waveform from the target object to be measured and from the reference substance, with such ultrasonic waves having been incident on the target object to be measured and on the reference substance through the base substrate; and in comprising a computing step for estimating the acoustic property distribution in the depth direction in consideration of the effect of the multiple reflections based on the impulse-response information of the ultrasonic waveform having been incident on the reference substance and based on the normalized impulse-response information having been obtained from the impulse-response information of the ultrasonic waveform having been incident on the target object to be measured; and in comprising a calculation step for calculating the thickness of at least one of the layers that constitute the skin based on the obtained acoustic-impedance distribution in the depth direction; and in comprising an evaluation step for evaluating a skin condition based on the thickness of the layer obtained in the calculation step.

(12) A skin-evaluation method according to means (11), characterized in that in the calculation step the thickness of the papillary layer constituting the skin is calculated based on the obtained acoustic-property distribution in the depth direction.

(13) A skin-evaluation method according to means (11) or (12), characterized in further comprising an image-construction step for constructing image data of an acoustic-property image based on the obtained acoustic-property distribution in the depth direction.

Effects of the Invention

As described above, in detail, the above means (1) to (10) of this invention provide an ultrasonic image-construction method, an ultrasonic image-construction apparatus and an ultrasonic image-construction program that can construct an ultrasonic tomographic image of a very thin object of a layered structure in a mode that makes it sensuously easy to understand such layered structure in a relatively simple way with a high degree of accuracy.

MODES FOR CARRYING OUT THE INVENTION

First Embodiment

Hereinafter, an ultrasonic skin-condition-evaluation apparatus, as the first embodiment embodying the ultrasonic image-construction method and is an apparatus of this invention, is described in detail in reference to FIGS. 1 to 15.

Figure 1:
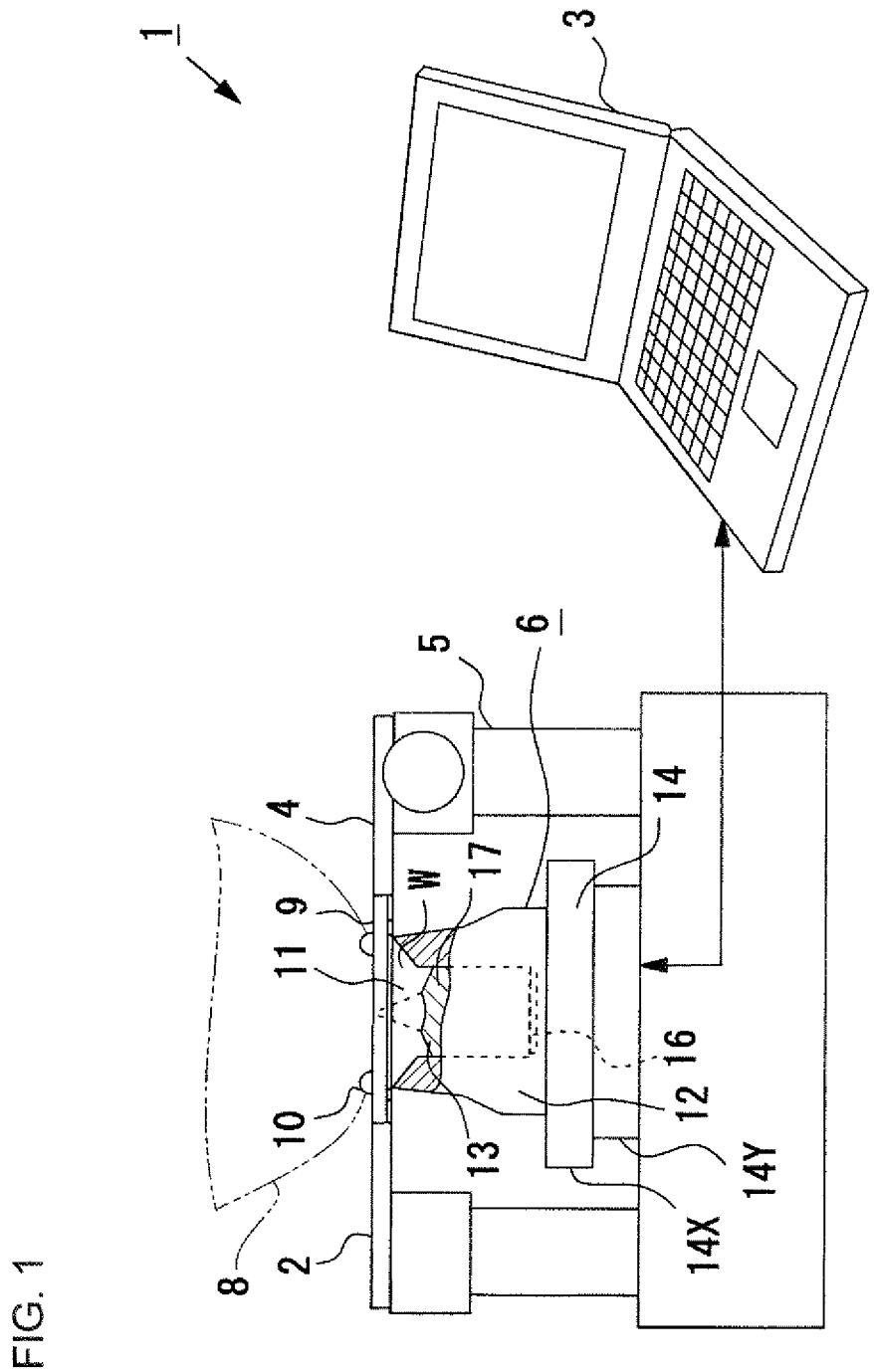
FIG. 1 is a schematic configuration diagram showing the ultrasonic skin-condition evaluation apparatus as the first embodiment of this invention.

FIG. 1 is a schematic configuration diagram showing an ultrasonic skin-condition-evaluation apparatus 1 as the embodiment of this invention. As shown in FIG. 1, the ultrasonic skin-condition-evaluation apparatus 1 of this embodiment comprises a pulse-excitation-type ultrasonic microscope 2 and a personal computer (PC) 3.

The pulse-excitation-type ultrasonic microscope 2 includes a microscope body 5 having a stage 4, and an ultrasonic probe 6 is provided below such stage 4. The ultrasonic probe 6 of the pulse-excitation-type ultrasonic microscope 2 is electrically connected to the PC 3.

The stage 4 of the embodiment is configured to be movable in the horizontal direction (that is, in the X direction and Y direction) by manual operation. A resin plate 9 is fixed on the stage 4. The stage 4 is fixed with a resin plate 9 for placing a human skin (living tissue) 8 as a target object to be measured in contact with the stage 4. A resin plate 9 is fixed on this stage 4 so that human skin (biological tissue) 8 as a target object is placed in contact with the stage 4. The human skin 8 should not necessarily be a piece of tissue, and in this embodiment a measurement or the like is performed by directly pressing a human cheek against the resin plate 9. Also, the resin plate 9, as a base substrate of known acoustic properties, is a flat-plate member that can transmit ultrasonic waves and is made of a material harder than that of the skin 8 that is a target object to be measured. When a member of such a shape and hardness is used as a base, it is possible surely and closely to place on the resin plate 9 the skin 8 as a target object to be measured, and it is possible to estimate accurately the acoustic-impedance distribution in the depth direction, thus improving the accuracy of the image construction. In this embodiment, a polystyrene plate of a thickness of 1.4 mm is used. Of course, it is also acceptable to use a plate made of a resin other than that of polystyrene.

On the resin plate 9, a reference member 10 (reference substance) is provided in advance on the upper surface of the side of such resin plate 9 where the skin 8 is placed in contact. The reference member 10 has known acoustic properties that are different from those of the resin plate 9. In this embodiment, for example, an acrylic resin (acrylic adhesive) is attached to the resin plate 9 to form the reference member 10. However, it is not limited to this. Any material other than a resin material (e.g. a glass material, a metal material, a ceramic material, etc.) may be used as the reference member 10 as long as such material can be brought into close contact with the reference member 10. Alternatively, instead of providing such a reference member 10, water for example or the like can be provided in contact with the upper surface of the resin plate 9 to use such water or the like as a reference substance. Also, in providing the reference member 10 on the resin plate 9 in advance, the impulse-response information of the ultrasonic waveform incident on the reference member 10 can be accurately and stably obtained without depending on the changes of the environment where the apparatus is placed.

The ultrasonic probe 6 includes a probe-main body 12 having a reservoir 11 capable of storing an ultrasonic-transmission medium W such as water or the like within its tip and includes an ultrasonic transducer 13 provided at—substantially the central portion of the probe-main body 12 and includes an X-Y stage 14 for scanning the probe-main body 12 two-dimensionally in the surface direction of the stage 4. The reservoir 11 of the probe-main body 12 has an upper opening, and the ultrasonic probe 6 is provided below the stage 4 with the opening of the reservoir 11 facing upward.

The ultrasonic transducer 13 is made of, for example, a zinc-oxide thin-film piezoelectric element 16 and a sapphire-rod acoustic lens 17. The ultrasonic transducer 13 irradiates the ultrasonic waves to the skin 8 and irradiates the reference member 10 from the lower-surface side of the resin plate 9 by being pulse excited. The ultrasonic wave that is irradiated by the ultrasonic transducer 13 is converged in a conical shape via the ultrasonic-transmission medium W of the reservoir 11 to be focused on the upper surface of the resin plate 9 (near the surface of the skin 8). Regarding the embodiment of this invention, an ultrasonic transducer 13 of a diameter of 1.2 mm, of a focal length of 1.5 mm, of a center frequency of 80 MHz and of a bandwidth of 50 to 105 MHz (−6 dB) is used.

Figure 2:
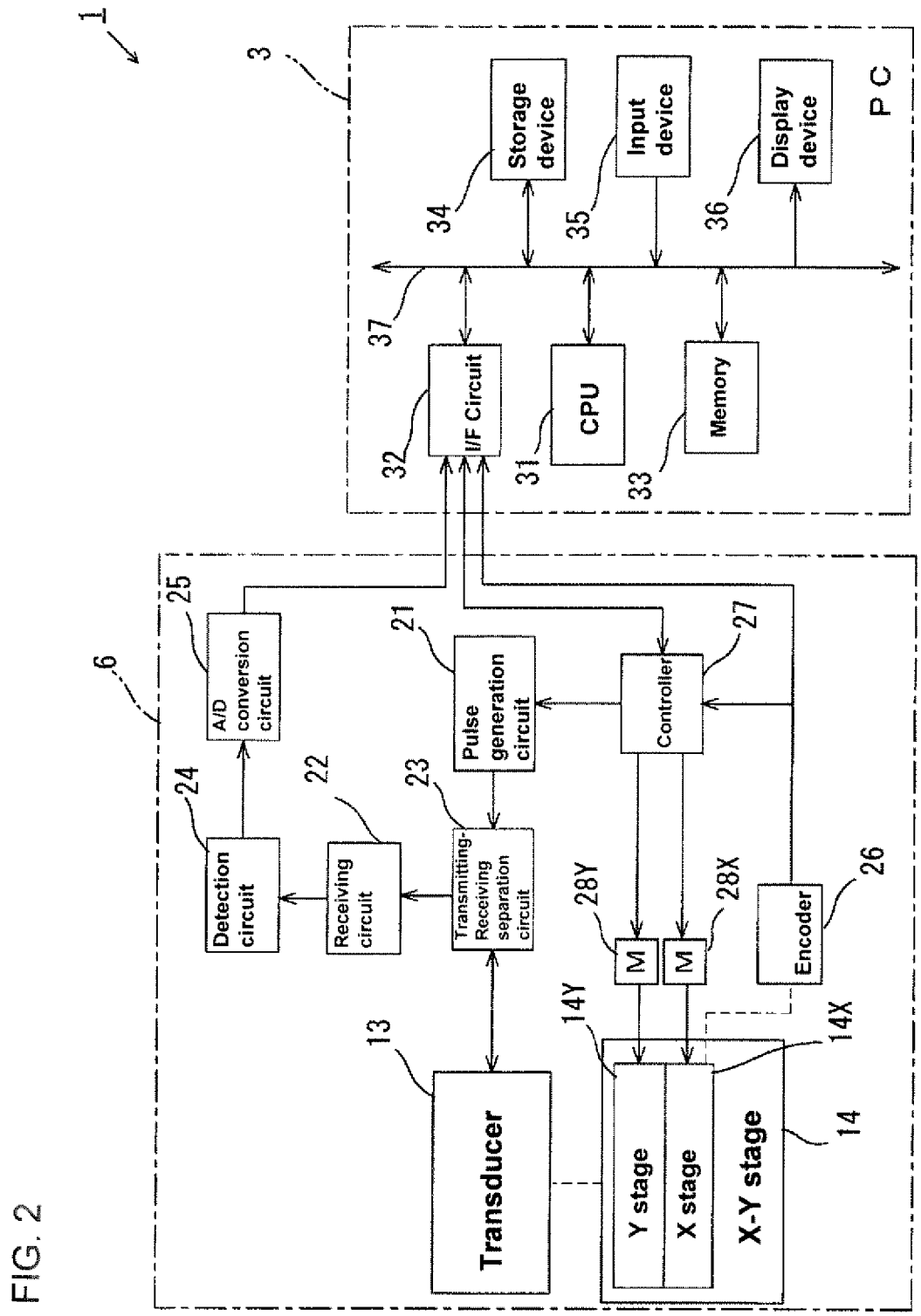
FIG. 2 is a block diagram showing the electrical constitution of the ultrasonic skin-condition evaluation apparatus as the first embodiment of this invention.

FIG. 2 is a block diagram showing the electrical configuration of the ultrasonic skin-condition-evaluation apparatus 1 as the embodiment of this invention.

As shown in FIG. 2, the ultrasonic probe 6 has an ultrasonic transducer 13, an X-Y stage 14, a pulse-generation circuit 21, a receiving circuit 22, a transmitting-and-receiving ultrasonic-wave-separation circuit 23, an ultrasonic-detection circuit 24, an A/D conversion circuit 25, an encoder 26 and a controller 27.

The X-Y stage 14 as the scanning means has an X stage 14X and a Y stage 14Y for two-dimensionally scanning an ultrasonic-irradiation point and has a motor 28X and a motor 28Y for driving the stages 14X and 14Y, respectively. Stepping motors and linear motors are used as these such motors 28X and 28Y.

A controller 27 is connected to each motor 28X and 28Y, and such motors are driven in response to a drive signal from the controller 27. The X stage 14X is continuously scanned (continuously fed) by driving these motors 28X and 28Y, and the Y stage 14Y is controlled to be intermittently fed, so that the X-Y stage 14 can be scanned at high speed.

Regarding the embodiment of this invention, an encoder 26 is provided corresponding to the X stage 14X, and the encoder 26 detects the scanning position of the X stage 14X. Specifically, when the scanning range is divided into 300× 300 measurement points (pixels), one scanning in the X direction (horizontal direction) is divided by 300. Then, the position of each measurement point is detected by the encoder 26 and taken into the PC 3. The PC 3 generates a drive-control signal in synchronization with the output of the encoder 26 to transmit the drive-control signal to the controller 27. The controller 27 drives the motor 28X based on this drive-control signal. Also, the controller 27 drives the motor 28Y once the scanning of one line in the X direction is completed based on the output signal of the encoder 26, and then the controller 27 moves the Y stage 14Y by one pixel in the Y direction.

Further, the controller 27 generates a trigger signal in synchronization with the drive-control signal, and then the controller 27 transmits such trigger signal to the pulse-generation circuit 21. As such, the pulse-generation circuit 21 generates an excitation pulse at the timing of synchronization with the trigger signal. As a result of the excitation pulse being supplied to the ultrasonic transducer 13 via the transmitting-and-receiving ultrasonic-wave-separation circuit 23, ultrasonic waves are emitted from the ultrasonic transducer 13.

Figure 3:
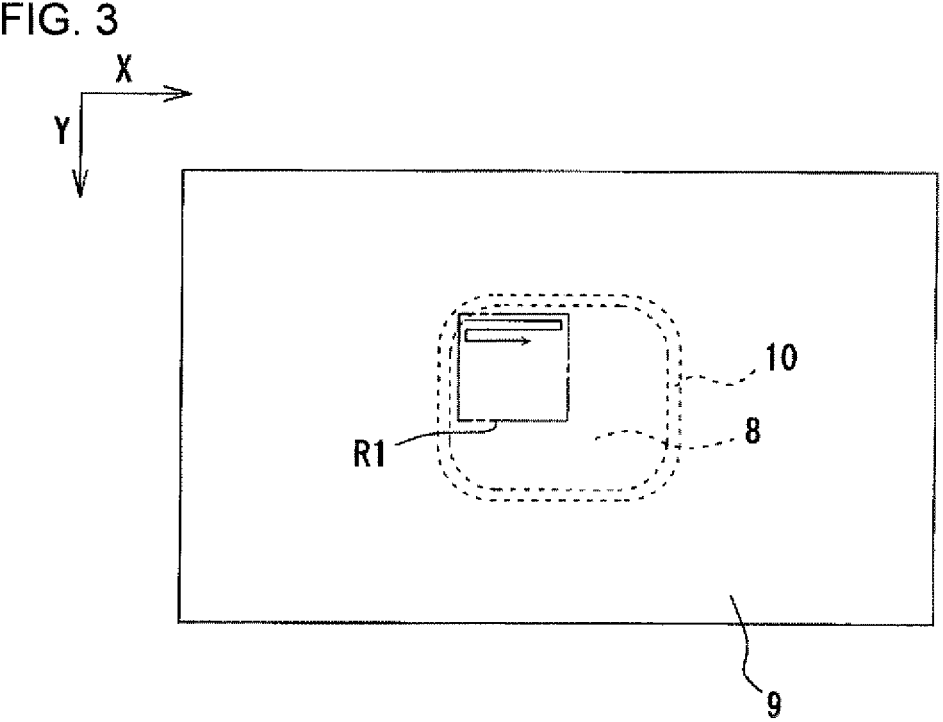
FIG. 3 is a schematic diagram showing an example of the scanning range of ultrasonic waves according to the movement of the X-Y stage.

FIG. 3 shows an example of the ultrasonic-scanning range R1 according to the movement of the X-Y stage 14. In this example, a reference member 10 is provided to surround the region where the skin 8 is placed in contact with such reference member 10. Then, scanning starts from the position where the reference member 10 is present in a state thereof the human skin 8 is pressed against such region. Then, as shown by the arrows (in FIG. 2), scanning is sequentially done two-dimensionally in the X direction and in the Y direction along the surface of the skin 8.

The thin-film piezoelectric element 16 of the ultrasonic transducer 13 is an ultrasonic transducer for both transmitting and receiving ultrasonic waves, and such ultrasonic transducer converts the ultrasonic waves (reflected waves) that are being reflected by the skin 8 into an electric signal. Then, the reflected-wave signal is transmitted to the receiving circuit 22 via the transmitting-and-receiving ultrasonic-wave-separation circuit 23. The receiving circuit 22 includes a signal-amplification circuit that amplifies the reflected-wave signal and outputs such amplified signal to the detection circuit 24.

The detection circuit 24 is a circuit for detecting reflected-wave signals from the skin 8 and includes a gate circuit (not shown). The detection circuit 24 of the present embodiment detects reflected-wave signals from the skin 8 and from the reference member 10 from among reflected-wave signals being received by the ultrasonic transducer 13. The reflected-wave signals being detected by the detection circuit 24 are then sent to the A/D conversion circuit 25 and subjected to A/D conversion and then transferred to the PC 3.

The PC 3 includes a CPU 31 (central-processing unit), an I/F circuit 32, a memory 33, a storage device 34, an input device 35 and a display device 36 that are connected to one another via a bus 37.

The CPU 31 executes a control program using the memory 33 and controls the entire system in an integrated manner.

The control program includes a program for controlling the two-dimensional scanning by the X-Y stage 14, a program for converting the reflected-signal-sequence data that is the basis of the ultrasonic B-mode echo image into an acoustic-impedance image, and includes a program for displaying an acoustic-impedance image, etc. In addition to the CPU31, a Digital Signal Processor (DSP), for example, can be provided within the CPU31 to perform a part of the signal processing that the CPU31 does.

The I/F circuit 32 is an interface (specifically, a USB interface) for transmitting and receiving signals between the ultrasonic probe 6 and controller 27. The I/F circuit 32 outputs the control signal (i.e. drive-control signal to be transmitted to the controller 27) to the ultrasonic probe 6 and then inputs transfer data (data transferred from the A/D conversion circuit 25 or the like) from the ultrasonic probe 6. When communicating the signals with the ultrasonic probe 6, the physical interface of the I/F circuit 32 is not limited to the above, but a wireless interface can also be used.

The display device 36 is, for example, a liquid crystal display, a plasma display, or an organic EL display (electroluminescence) or the like. The display device 36 can be used weather it is a color display or a monochrome display but a color display is preferred. The display device 36 is used for displaying the acoustic-impedance image of the surface layer of the skin 8 and for displaying the input screen for various settings.

The input device 35 is an input-user interface such as a touch panel, a mouse, a keyboard, a pointing device or the like and is used for inputting requests, instructions and parameters from the user.

The storage device 34 is a hard-disk drive such as a magnetic-disk device, an optical-disk device or the like and stores various control programs and various data. The memory 33 includes a Random Access Memory (RAM) and a Read Only Memory (ROM) and stores the reflected waveform of the reference member 10 acquired in advance for the ultrasonic measurement and its acoustic impedance. The CPU31 transfers programs and data from the storage device 34 to the memory 33 according to the instructions from the input device 35 and executes them sequentially. Also, the program executed by the CPU31 may be a program stored in a storage medium such as a memory card, a flexible disk, an optical disk, a program or the like that is downloaded via a communication medium. Each program should be used after installing it in the storage device 34.

Next, regarding the ultrasonic skin-condition-evaluation apparatus 1 as the embodiment of this invention, a method for constructing an acoustic-impedance image from a reflected-signal sequence that is the basis of an ultrasonic B-mode echo image is described.

This ultrasonic skin-condition-evaluation apparatus 1 obtains impulse-response information, which is normalized, from the impulse-response information of an ultrasonic waveform incident on the reference member 10 as a reference substance and from the impulse-response information of an ultrasonic waveform incident on the skin 8 as the target object; and then estimates the acoustic-property distribution in the depth direction in consideration of the multiple reflections based on the normalized impulse-response information. Also, to perform such an estimation, assuming that in the calculation step the lossless micro-transmission paths 51 of different acoustic impedances are connected in the depth direction to form an assembly of micro-transmission paths 51 within the target object, a calculation to estimate the acoustic property (i.e. acoustic-impedance distribution) in the depth direction of the transmission path is done by sequentially repeating the process of estimating the acoustic impedance of the micro-transmission path 51 adjacent to the back side based on the estimated result of the acoustic impedance of the micro-transmission path 51 on the front side. Such a calculation is executed based on a predetermined algorithm having been stored in the memory 33.

This algorithm is an algorithm for estimating the acoustic-impedance distribution in the depth direction by using a reflected-signal sequence that is the basis of an ultrasonic B-mode echo image. This algorithm refers to the principle of the time-domain-reflection-measurement method (Time Domain Reflectometry (TDR) method) and is also an algorithm for converting a reflected-signal sequence, which is the source of the ultrasonic B-mode echo image, into an acoustic-impedance image in the depth direction through an analysis of the time-frequency domain in consideration of the multiple reflections within the skin tissue. This will be specifically described, below.

Figure 4A:
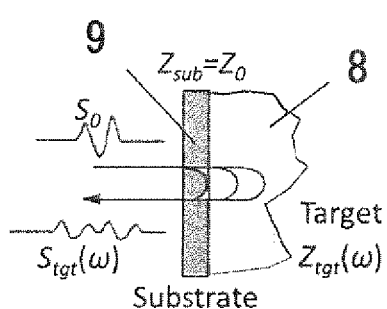
FIG. 4(a) is an explanatory drawing of the acquisition of a reflected waveform from a target object to be measured when the actual measurement is being done.
Figure 4B:
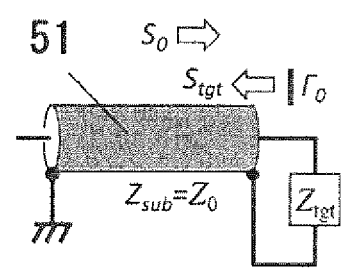
FIG. 4(b) is an explanatory drawing about the acquisition of a reflected waveform when assuming that the target object to be measured is a micro-transmission path.

FIG. 4(*a*) is a drawing explaining the acquisition of the reflected waveform from a target object to be measured when the actual measurement is done. FIG. 4(*b*) is a drawing explaining the acquisition of a reflected waveform when assuming that the target object to be measured is a micro-transmission path. FIG. 5(*a*) is a drawing explaining the acquisition of a reflected waveform from a reference substance when the actual measurement is done. FIG. 5(*b*) is a drawing explaining the acquisition of the reflected waveform when assuming that the reference substance is a micro-transmission path.

Firstly, as shown in FIG. 4(*a*), the ultrasonic transducer 13 is activated, causing an ultrasonic-convergent beam of a depth of focus sufficient for the target object to be transmitted through the resin plate 9 as the base substrate. Then, a convergent beam of ultrasonic waves is incident onto the skin 8 as the target object, and a reflected waveform therefrom is thus acquired. The impulse response $\Gamma_0(\omega)$ of such convergent beam of ultrasonic waves at this time is expressed by the following Formula 1 from the incident wave $S_0$ and the reflected wave $S_{tgt}(\omega)$ from the skin 8 using the Fourier transformation.

[Formula 1]
$$\Gamma_0(\omega) = \frac{S_{tgt}(\omega)}{S_0} \qquad (1)$$

In this case, it is necessary to obtain a reflected waveform from the reference member 10 that has a known and uniform acoustic impedance as well as being of sufficient thickness compared to that of the target object. The reflected wave $S_{ref}(\omega)$ from the reference member 10 is expressed by the following Formula 2 using the acoustic impedance $Z_{ref}$ of the reference member 10 and the acoustic impedance $Z_0$ of the resin plate 9.

[Formula 2]
$$S_{ref}(\omega) = \frac{Z_{ref} - Z_0}{Z_{ref} + Z_0} S_0 \qquad (2)$$

Further, the impulse response $\Gamma_0(\omega)$ from the skin 8 as the target object is expressed by the following Formula 3. However, since the impulse response $\Gamma_0(\omega)$ includes reflections generated from a plurality of interfaces behind the tissue of the skin 8, the impulse response $\Gamma_0(\omega)$ has frequency characteristics. Thus, the normalized impulse-response information is obtained from the impulse-response information of the ultrasonic waveform incident onto the reference substance, and the impulse-response information of the ultrasonic waveform incident onto the measurement object is obtained by the referenced Formulae, above.

[Formula 3]

$$\Gamma_0(\omega) = \frac{Z_{ref} + Z_0}{Z_{ref} - Z_0} \cdot \frac{S_{tgt}(\omega)}{S_{ref}(\omega)} \quad (3)$$

Figure 6:
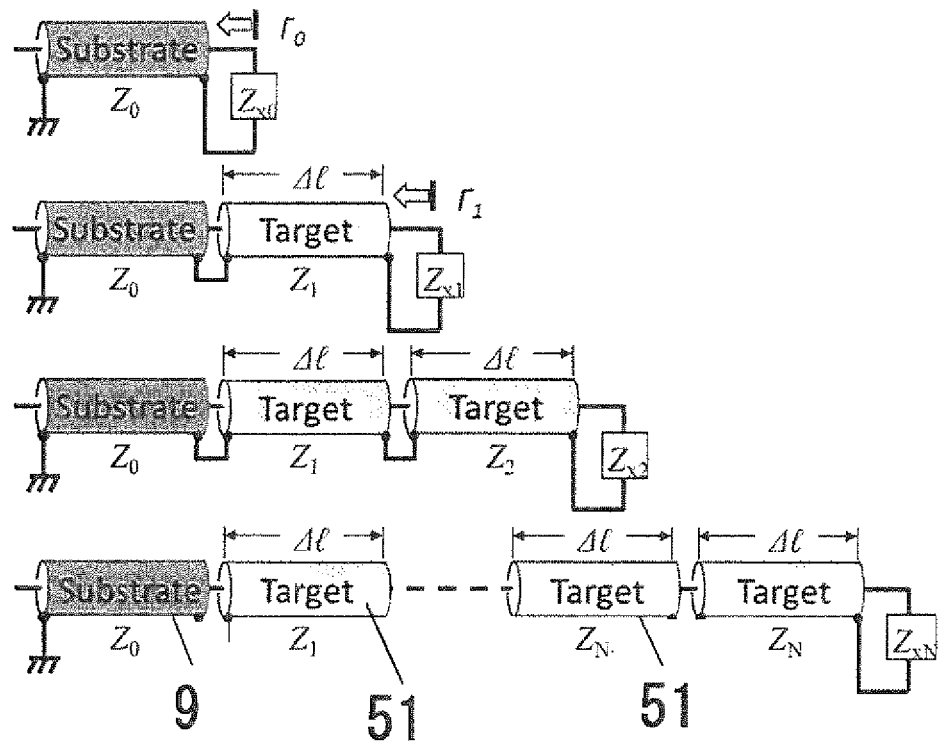
FIG. 6 is a diagram conceptually showing how the characteristic impedance of each micro-transmission path is estimated.

Here, FIG. 6 is a diagram conceptually showing the state in which the characteristic impedances $Z_1, Z_2, \ldots Z_n$ of each micro-transmission path 51 are estimated, in order, from the micro-transmission path 51 in contact with the resin plate 9. As shown in this diagram, the characteristic impedances $Z_1, Z_2 \ldots Z_n$ of each micro-transmission path are estimated, in order, from the micro-transmission path 51 in contact with the resin plate 9 in the depth direction.

Figure 7:
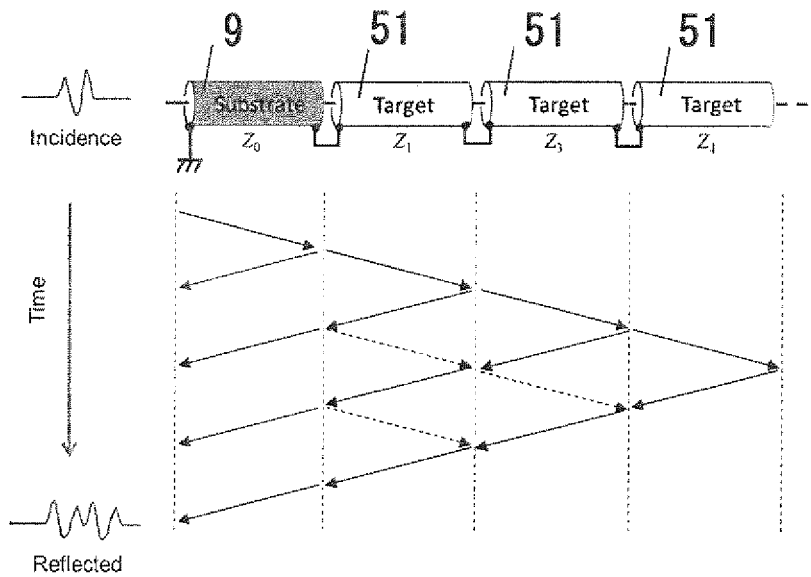
FIG. 7 is a diagram conceptually showing the effect of multiple reflections.

FIG. 7 is a diagram conceptually showing the effect of multiple reflections. The following Formula 4 represents $g_0(t)$ obtained by inverse Fourier transformation of the impulse response $\Gamma_0(\omega)$, but the first term is not effected by such multiple reflections (see FIG. 7). Therefore, the characteristic impedance Z1 of the micro-transmission path 51 in contact with the resin plate 9 can be estimated from the value of the first term as shown in the following Formula 5.

[Formula 4]

$$g_0(t) = IFT(\Gamma_0(\omega)) \quad (4)$$

[Formula 5]

$$Z_1 = \frac{1 + g_0(t_0)}{1 - g_0(t_0)} Z_0 \quad (5)$$

The acoustic impedance $Z_{x0}$ of the skin 8 in the frequency domain is expressed by the following Formula 6 by using $\Gamma_0$.

[Formula 6]

$$Z_{x0} = \frac{1 + \Gamma_0}{1 - \Gamma_0} Z_0 \quad (6)$$

$Z_{x0}$ is also expressed by the following Formula 7 by using the impulse response $\Gamma_1$ from further behind

[Formula 7]

$$Z_{x0} = \frac{1 + \Gamma_1 e^{-2\gamma \Delta l}}{1 - \Gamma_1 e^{-2\gamma \Delta l}} Z_1 \quad (7)$$

Hereinafter, as described in the following Formulae 8 and 9, $\gamma$ is the propagation constant, $\alpha$ is the attenuation constant, $\beta$ is the phase constant and f is frequency. However, in the conversion algorithm of the embodiment of this invention, it is assumed that $\alpha=0$, and that the sonic speed of all of the micro-transmission paths 51 of the skin 8 is c=1,600 (m/s).

[Formula 8]

$$\gamma = \alpha + j\beta \quad (8)$$

[Formula 9]

$$\beta = \frac{2\pi f}{c} \quad (9)$$

Also, here the distance $\Delta l$ of each micro-transmission path 51 is expressed by the following Formula 10, and the sonic speed is assumed to be c=1,600 (m/s). The distance $\Delta t$ corresponds to one point of the sampling interval of the reflected waveform from the skin 8 ($\Delta t$=2 (ns) in this embodiment).

[Formula 10]

$$\Delta l = c\Delta t \quad (10)$$

Then, based on the above formula, the impulse response $\Gamma_1$ from the micro-transmission path 51 that is located deeper can be obtained (see the following Formula 11). In other words, the value of $\Gamma_1$ at the end-point of $Z_1$ can be estimated based on the values of $Z_{x0}$ and $Z_1$.

[Formula 11]

$$\Gamma_1 = \frac{Z_{x0} - Z_1}{Z_{x0} + Z_1} e^{2\gamma \Delta l} \quad (11)$$

Formula 12, below, expresses $g_1(t)$ that is obtained by the inverse Fourier transformation of the impulse response $\Gamma_1(\omega)$, and the first term is not affected by multiple reflections. Accordingly, it is possible to estimate, based on the value of the first term, the characteristic impedance $Z_2$ of the further micro-transmission path 51 adjacent to the micro-transmission path 51, and it is possible to estimate $Z_{x1}, \Gamma_2(\omega)$. (See Formulae 13, 14 and 15).

[Formula 12]

$$g_1(t) = IFT(\Gamma_1(\omega)) \quad (12)$$

[Formula 13]

$$Z_2 = \frac{1 + g_1(t_0)}{1 - g_1(t_0)} Z_1 \quad (13)$$

[Formula 14]

$$Z_{x1} = \frac{1 + \Gamma_1}{1 - \Gamma_1} Z_1 = \frac{1 + \Gamma_2 e^{-\gamma \Delta l}}{1 - \Gamma_2 e^{-2\gamma \Delta l}} Z_2 \quad (14)$$

[Formula 15]

$$\Gamma_2 = \frac{Z_{x1} - Z_2}{Z_{x1} + Z_2} e^{2\gamma \Delta l} \quad (15)$$

By repeating this process, the characteristic impedances (acoustic impedances) $Z_1, Z_2, \ldots Z_n$ of each micro-transmission path 51 can be estimated. Based on these estimated results, the acoustic-impedance distribution in the depth direction of the transmission path is estimated, and finally the reflected-signal sequence that is the basis of the B-mode echo image is converted into an acoustic-impedance image.

Next, the calculating process, executed by the CPU31 as the processor, to construct an acoustic-impedance image in the ultrasonic skin-condition evaluation apparatus 1 as the embodiment of this invention, will be described with reference to the flowchart of FIG. 8.

Firstly, the human-cheek skin 8, as the target object, is pressed and placed in contact with the upper surface of the resin plate 9. In this state, first, the initial operation of the ultrasonic probe 6 is performed. In other words, by operating the controller 27 based on instruction from the CPU31, the motors 28X and 28Y are driven, and the X-Y stage 14 is moved, so that the reference member 10 is irradiated with ultrasonic waves at a certain position.

Figure 5A:
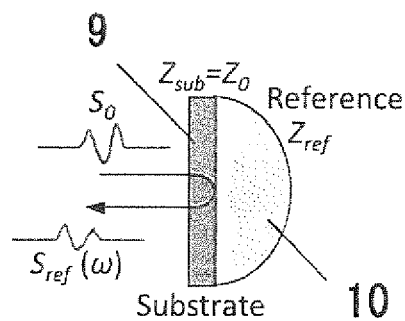
FIG. 5(a) is an explanatory drawing of the acquisition of a reflected waveform from a reference substance when an actual measurement is being done.
Figure 5B:
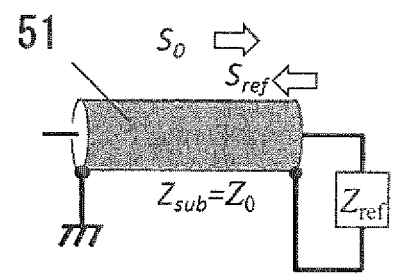
FIG. 5(b) is an explanatory drawing of the acquisition of a reflected waveform when assuming that the reference substance is a micro-transmission path.

At this time, when an excitation pulse is supplied to the transducer 13 based on instruction from the CPU31, as shown in FIG. 5(a), the reference member 10 is irradiated by the ultrasonic wave $S_0$, and the reflected wave $S_{ref}(\omega)$ is detected by the detection circuit 24 via the receiving circuit 22.

Thereafter, motors 28X and 28Y are driven by the controller 27 based on instruction from the CPU31, and then two-dimensional scanning by the X-Y stage 14 is started. The CPU31 acquires the coordinate data of the measurement point based on the output of the encoder 26 (step S110).

As shown in FIG. 4(a), an excitation pulse is sent to the transducer 13 based on instruction from the CPU31. Then, the ultrasonic wave $S_0$ is irradiated onto the cheek skin 8. Thereby, the reflected wave $S_{tgt}(\omega)$ is detected by the detection circuit 24 via the receiving circuit 22. The CPU31, as the reflected-wave-acquisition means, then acquires the digital data converted by the A/D conversion circuit 25 via the I/F circuit 32, and such e digital data is associated with the coordinated data as the impulse-response data of the ultrasonic waveform from the cheek skin 8 and is then stored in the memory 33 (step S120).

Next, the CPU31, as the computing means, executes a predetermined calculation based on the above conversion algorithm with reference to the principle of the TDR method, using the acquired impulse-response-signal data. Then, the CPU31 estimates the acoustic-impedance distribution in the depth direction at the measurement point on the cheek skin 8 by calculation and then stores the estimated result in the memory 33 in association with the coordinate data (step S130).

Thereafter, the CPU31, as the image-construction means, performs image processing for constructing an acoustic-impedance image (tomographic image) based on the estimated result of the acoustic-impedance distribution (step S140). Specifically, the CPU31 performs color-modulation processing, based on the estimated result of the acoustic-impedance distribution, and constructs image data displayed in different colors according to the magnitude of the acoustic impedance, thus storing the image data in the memory 33.

Then, the CPU31 completes the processing of all of the measurement points and determines whether the image data has been acquired from all of the measurement points or not (step S150). If all of the data has not been acquired (step S150) then "NO" appears on the display, and the CPU31 returns to step S110 and repeats the processes of steps S110 to S140. If all of the data has been acquired (step S150) then "YES" appears on the display, and the CPU31 proceeds to the next step S160.

Figure 8:
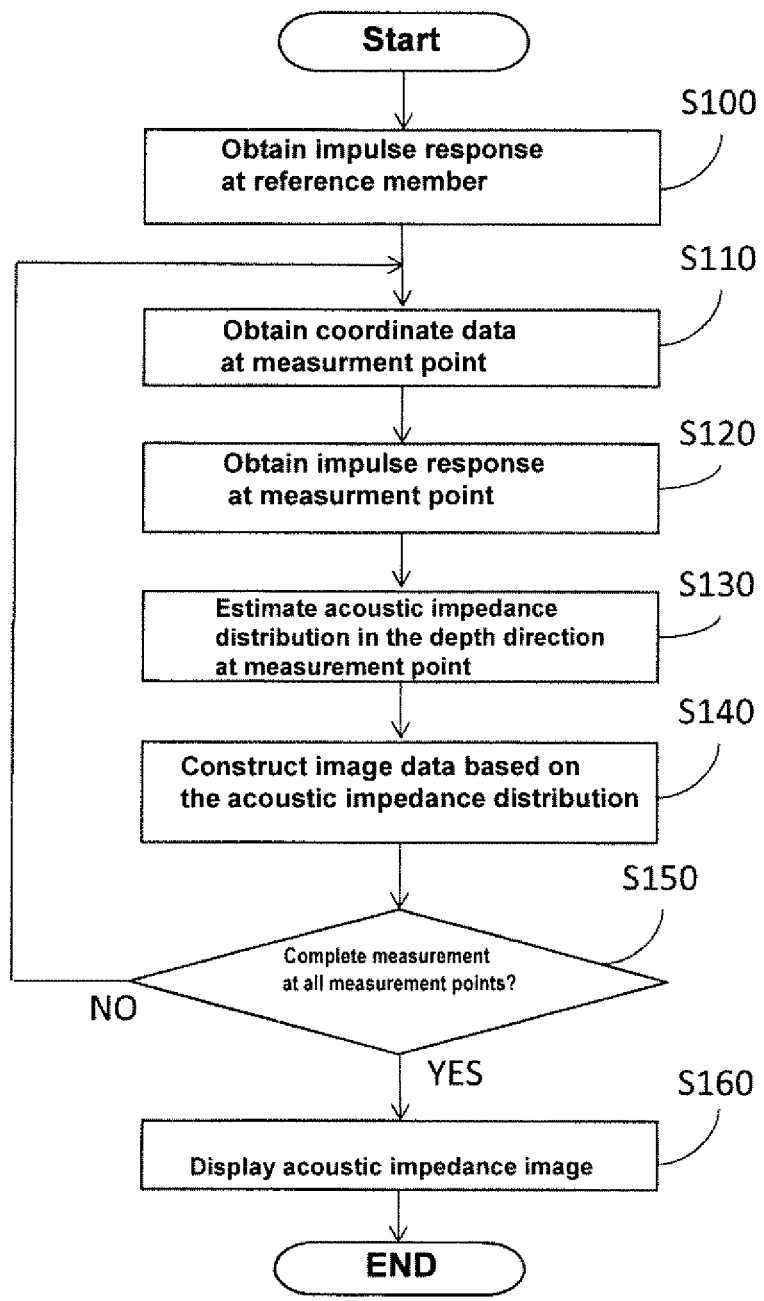
FIG. 8 is a flowchart explaining the calculating process for constructing an acoustic-impedance image in the first embodiment of this invention.

Then, the CPU31 transfers the data to the display device 36 and displays the acoustic-impedance image (tomographic image) that is present on a predetermined straight line (step S160), thus completing the processing as shown in FIG. 8. After such a series of processes, an acoustic-impedance image (tomographic image), which is color-coded according to the magnitude of the acoustic impedance at the cheek skin 8, is displayed. For example, by visually observing such cheek skin 8, the condition of it can then be evaluated.

Embodiment

Figure 9A:
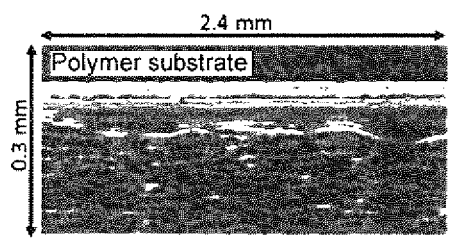
FIG. 9(a) is an ultrasonic B-mode echo image before conversion.
Figure 9B:
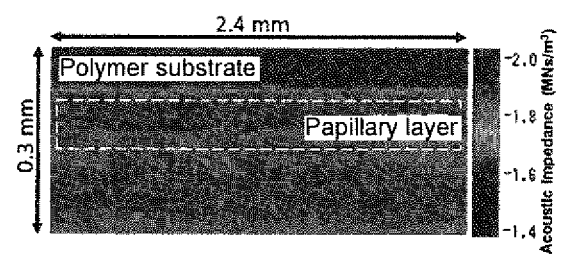
FIG. 9(b) is an acoustic-impedance image after conversion.

Hereinafter, examples that more specifically embodies this invention are described. In this embodiment, persons in their 20's to 60's are tested, and their cheek skin 8 as the target object was visually observed with the naked eye by converting the reflected-signal sequence from the cheek skin 8 being irradiated with the convergent ultrasonic waves into an acoustic-impedance image using the above conversion algorithm. FIG. 9(a) shows an ultrasonic B-mode echo image before conversion. FIG. 9(b) shows an acoustic-impedance image after conversion. Regarding the embodiment of this invention, the measurement was done under the condition thereof the measurement range is 2.4 mm×2.4 mm, the measurement points are 300 (X direction)×150 (Y direction)×200 (Z direction; depth direction), and the sampling time of each measurement point is 2 ns.

Figure 10:
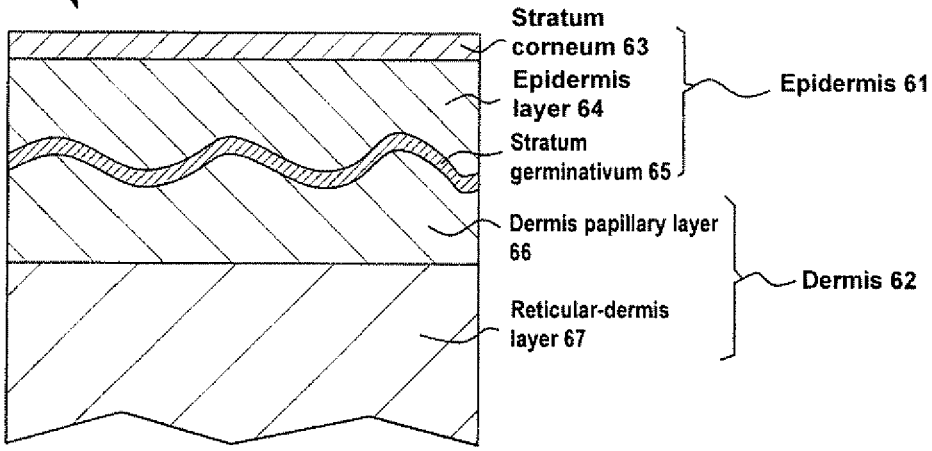
FIG. 10 is a schematic cross-sectional view showing the layered structure of human-cheek skin.

FIG. 10 is a schematic cross-sectional view of the layered structure of the skin 8 of a human cheek. The skin 8 is formed by an epidermis 61, by a dermis 62 and by subcutaneous tissue (not shown). The stratum corneum 63 is the outermost surface layer of the epidermis 61, and the epidermis layer 64 and stratum germinativum 65 are located beneath the stratum corneum 63, toward the deeper layer of the skin 8. The dermis 62 is of the (dermis) papillary layer 66 and reticular-dermis layer 67, which are in contact with the stratum germinativum 65.

Figure 11A:
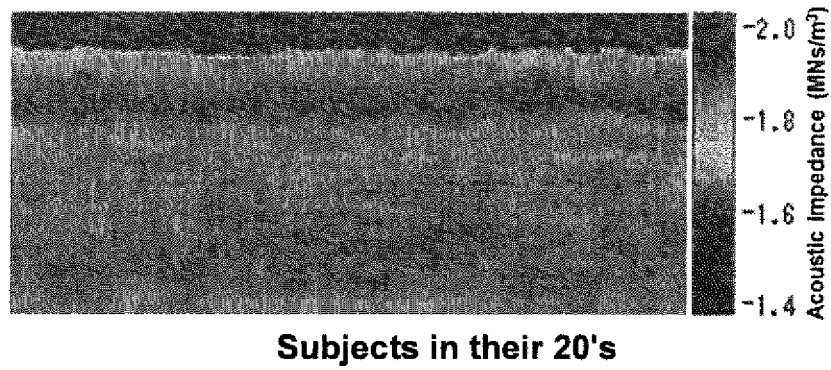
FIGS. 11(a) to 11(c) are acoustic-impedance images of the cheeks of subjects in their 20's, 40's and 60's, respectively.
Figure 11B:
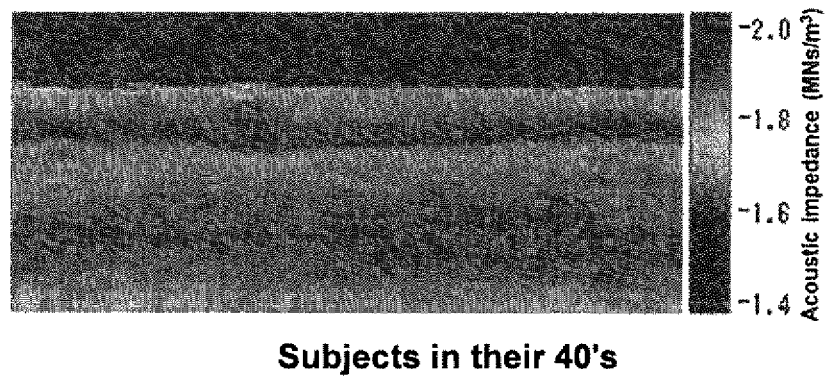
Figure 11C:
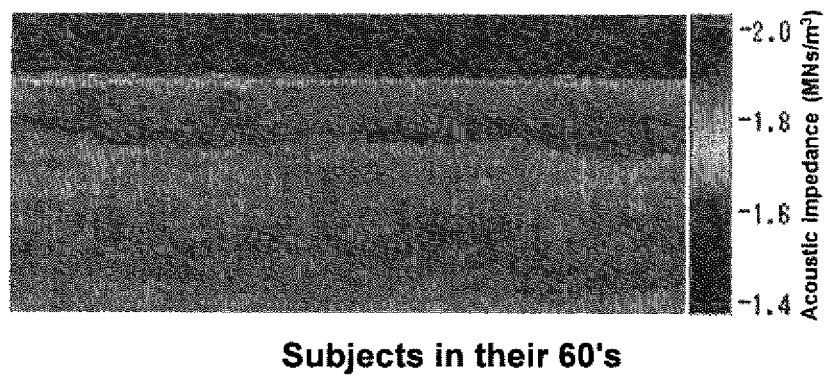

In comparing the ultrasonic B-mode echo image as shown in FIG. 9(a) with the acoustic-impedance image as shown in FIG. 9(b), it is seen that speckle noise had been generated in the former image due to the effect of multiple reflections, and that the former image had been considerably disturbed. On the other hand, the latter image is more quantitative than the former image, and it is seen that the latter image had reduced the effect of multiple reflections. Also, as shown in FIG. 9(b), when the post-converted acoustic-impedance image was observed, a tomographic image that markedly represented the anatomical features on a human cheek was obtained. Among such anatomical features, a layer of skin of particularly low acoustic impedance was identified. Furthermore, since the thickness of this layer of skin was different for each subject and seemed to be less thick with age, this layer was assumed to be a "papillary layer 66," and such thickness was analyzed. FIG. 11(a) shows an acoustic-impedance image of the cheek of a subject in his 20's; FIG. 11(b) shows an acoustic-impedance image of the cheek of a subject in his 40's; FIG. 11(c) shows an acoustic-impedance image of the cheek of a subject in his 60's.

Figure 12:
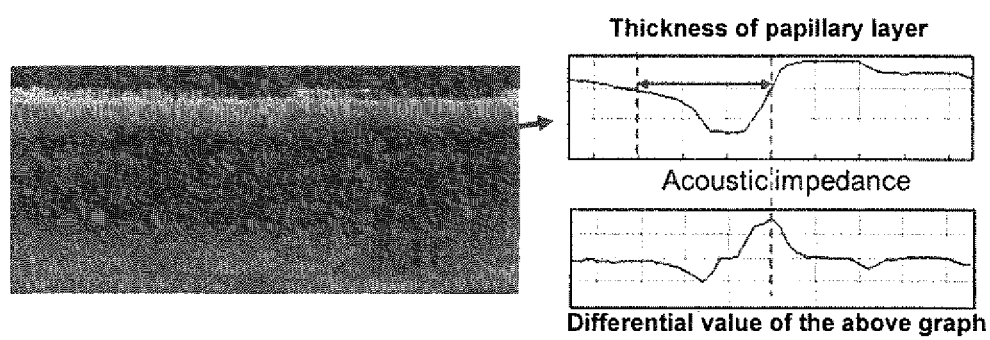
FIG. 12 is a graph showing the differential value of the profile of acoustic impedance.
Figure 13:
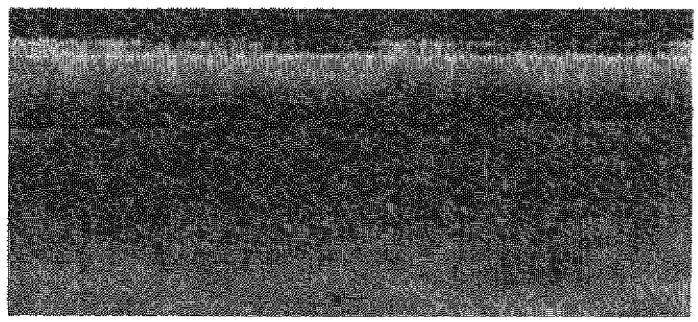
FIG. 13 is an acoustic-impedance image plotting the position of the papillary layer detected by the method as shown in FIG. 12.

For the calculation of the thickness of the papillary layer 66 as shown in FIG. 12, a differential value of the acoustic-impedance profile was used. The position of the steepest slope of the acoustic-impedance profile is detected from this differential value (the position is seen in the broken line in the center of the graph as shown in FIG. 12), and such differential value was defined as that distance between the points that becomes equal to that value (the distance between the broken lines on the left side of the graph as shown in FIG. 12) as the thickness of the papillary layer 66. FIG. 13 shows an image of which the position of the papillary layer 66 that was detected by this method is plotted.

Figure 14:
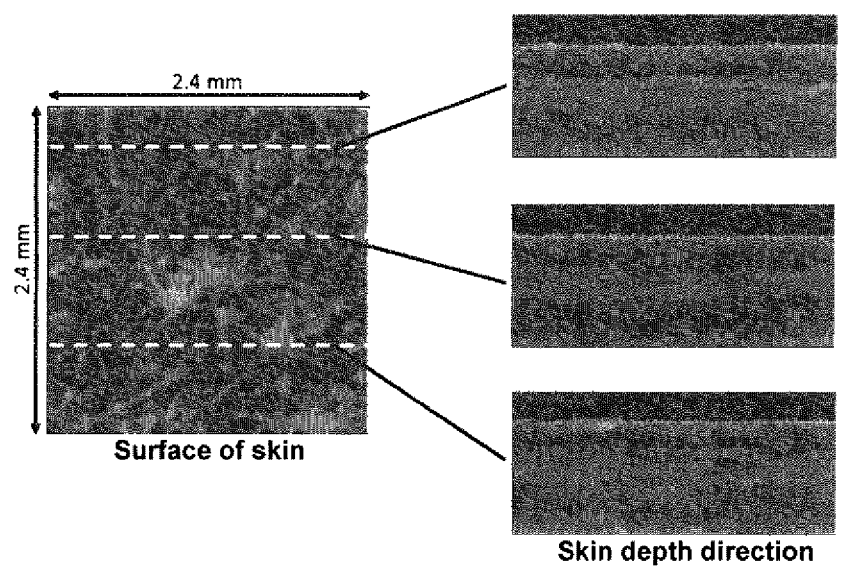
FIG. 14 shows three arbitrary acoustic-impedance images selected from one of the subjects.

Using this technique, three acoustic-impedance images were arbitrarily selected from one subject as shown in FIG. 14, and the average thickness of these papillary layers 66 was calculated.

Figure 15:
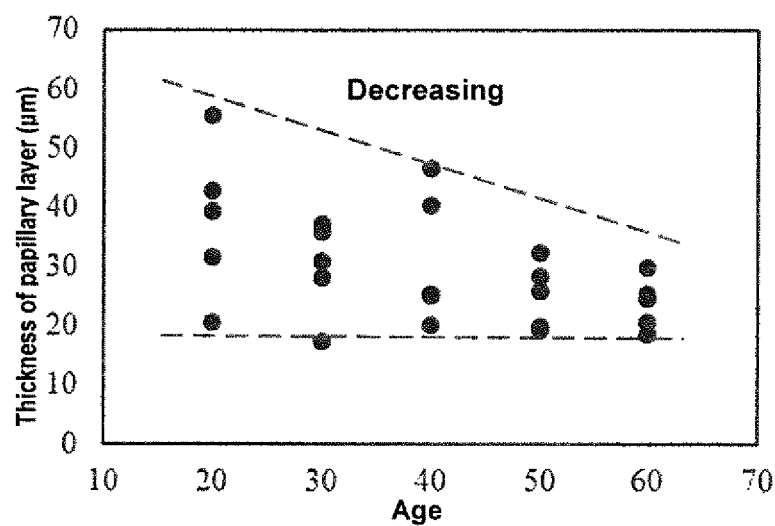
FIG. 15 is a graph showing the results of comparing the average thickness of the papillary layer of each age group.

Then, of 25 subjects in their 20's to 60's, the average thickness of the papillary layer 66 was compared regarding each age group by the above method. The result of such comparison by age is shown in the graph of FIG. 15.

According to this comparison by age, it was confirmed that the average thickness of the part considered to be the papillary layer 66 and the individual differences (thickness variations) tend to decrease with age.

From the result it of this comparison, these facts as follows were considered. That capillaries and terminal nerves are concentrated in the papillary layer 66, and that nutrition is supplied from this layer to the above epidermis 61. Therefore, the papillary layer 66 is considered to be an important part of the skin that effects the texture of the skin. It was reported in the past that the papillary layer 66 is flattened with age. In this respect such a past report agreed with the analysis result of the average thickness of the papillary layer 66. Also, it was seen that even younger subjects in their 20's and 30's are suffering from a thin papillary layer 66. For this reason, there are two types of skin aging that is associated with sunburn and with age itself, and it was presumed that even younger generations suffer from a flattened papillary layer 66 by sunburn. In addition, the acoustic impedance decreased at the portion of skin assumed to be the papillary layer 66, and that such acoustic impedance increased in the deeper portion of skin. For this reason, it was presumed that the collagen of the dermal-papillary layer 66 is thin and of low-oriented fibers, unlike the reticular-dermis layer 67, so that the sound velocity of the dermal-papillary layer 66 is lower than that of the reticular-dermis layer 67. As a result of the above comparison test, it was concluded that it is possible to confirm the papillary layer 66 by estimating the acoustic-impedance distribution in the depth direction from the reflected signal sequence that is the basis of the ultrasonic B-mode echo image, thereby constructing a tomographic image.

Therefore, according to the embodiments of this invention, the following effects can be obtained.

(1) In the ultrasonic skin-condition-evaluation apparatus 1 as the embodiment of this invention, the normalized impulse-response information, that is, the independent impulse-response information, without depending on the changes of the environment where the apparatus is placed, is obtained from the impulse-response information of the ultrasonic waveform incident on the reference member 10 and from the impulse-response information of the ultrasonic waveform incident on the skin 8. Based on the normalized impulse-response information, calculation is performed to estimate the acoustic-property distribution in the depth direction in consideration of the effect of multiple reflections. As a result, an ultrasonic-tomographic image of a very thin skin 8 having a layered structure can be constructed relatively easily with high degree of accuracy as an acoustic-impedance image in which the layered structure can be sensuously understood. Also, the acoustic-impedance image obtained by this apparatus 1 is color-coded and imaged information of each absolute value of the estimated acoustic impedance, wherein such color-coded and imaged information is the cross-sectional distribution (depth distribution) information of the dynamic characteristics for each layer without cutting the target object to be measured (i.e. non-invasively).

Herein, an ultrasonic B-mode echo image generally obtained by a normal ultrasonic-diagnostic apparatus can show at any rate the layer information inside a biological tissue such as the skin 8 or the like. However, such image of the layer information is a reflected image from the interface between the layers having a difference of a certain degree or more in the acoustic impedance. In other words, once the difference in acoustic impedance is reduced to a certain extent, it was extremely difficult to form an image that reflects the structure of the interface even if such an interface exists histogenetically. Therefore, a general-reflection image was insufficient to understand the reflection image (difference in acoustic impedance) inside a biological tissue that reflects the internal structure and fine layered structure of such biological tissue. Contrarily, the ultrasonic skin-condition-evaluation apparatus 1 of this invention allows for clearly showing the layered structure of the skin 8 based on the dynamic-characteristic distribution that could not be detected at all by the conventional ultrasonic B mode, thus making it possible to understand such layered structure as a clear tomographic image with sufficient resolution. In addition, since such a clear tomographic image cannot be obtained by other non-invasive visualization apparatuses (e.g. an optical-coherence-tomography apparatus (OCT), an in vivo confocal microscope or the like), it is tremendously significant to have embodied this ultrasonic skin-condition-evaluation apparatus 1. As described above, the ultrasonic skin-condition-evaluation apparatus 1 as the embodiment of this invention allows for evaluating the condition of the skin 8 (the condition relating to the dynamic characteristics of each layer of the skin 8) easily and non-invasively.

(2) By the ultrasonic skin-condition-evaluation apparatus 1 as the embodiment of this invention, ultrasonic waves are incident on the target object to be measured while relatively scanning in a two-dimensional direction. Therefore, as shown in FIG. 14, tomographic images at a plurality of positions can be obtained reliably and relatively easily.

(3) The ultrasonic skin-condition-evaluation apparatus 1 as the embodiment of this invention employs the method for converting the reflected-signal sequence that is the basis of the ultrasonic B-mode echo image into the acoustic impedance in the depth direction through a time-frequency domain analysis in consideration of the multiple reflections in the skin tissue, thus making it possible relatively easily to perform the predetermined calculation. Moreover, the embodiment of this invention, using the conversion algorithm mentioned above, performs the calculation to estimate the acoustic-impedance distribution in the depth direction of the micro-transmission path 51 by sequentially repeating the process of estimating such acoustic impedance of the micro-transmission path adjacent to the back side based on the estimated result of the acoustic impedance of the micro-transmission path on the front side.

Second Embodiment

Hereinafter, an ultrasonic skin-condition-evaluation apparatus 1 as the second embodiment that embodies the ultrasonic-image-construction method and its apparatus of this invention will be described in detail with reference to FIG. 16. Also, regarding the structure that is common with the structure of the aforementioned first embodiment, detailed description is omitted instead of indicating the reference numbers of the same member.

Figure 16:
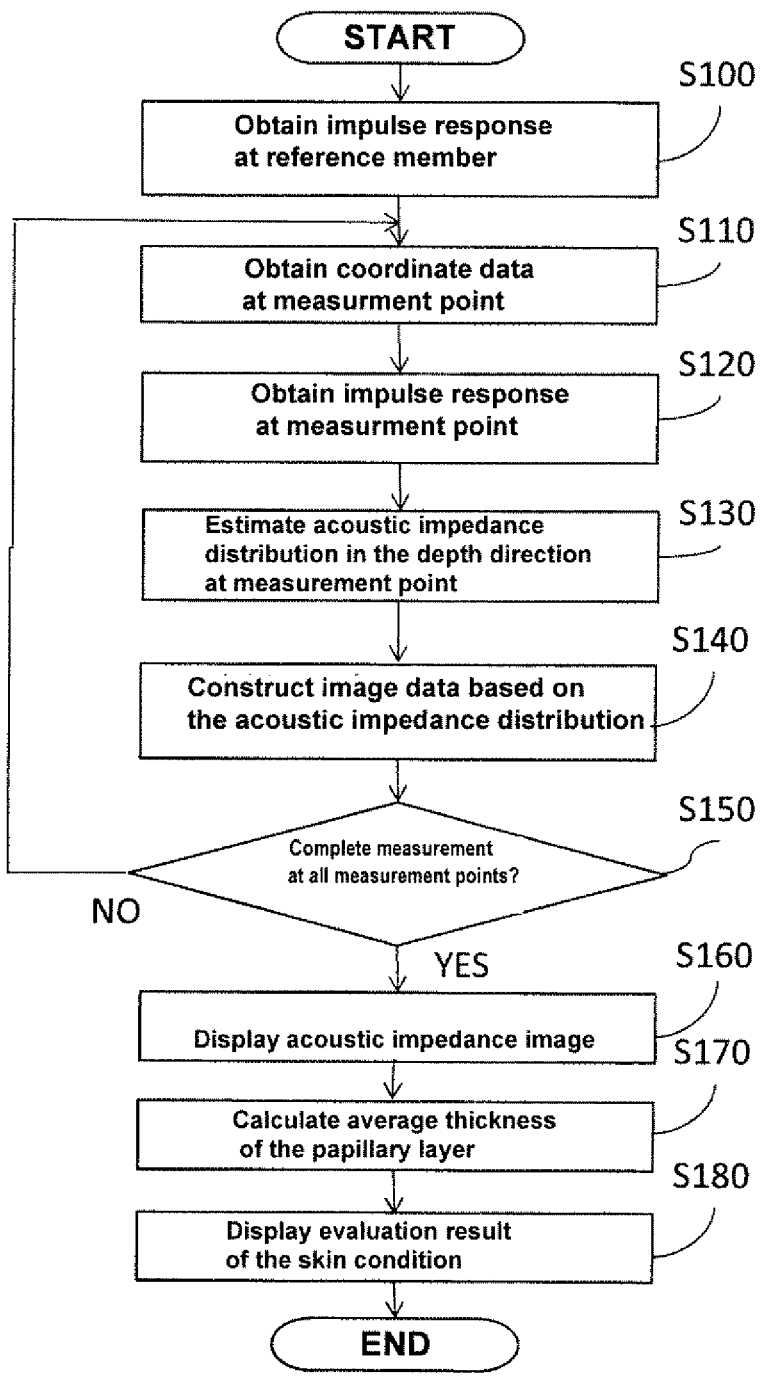
FIG. 16 is a flowchart for explaining the calculating process on the construction of an acoustic-impedance image and on the evaluation of a skin condition as the second embodiment of this invention.

As shown in the flowchart of FIG. 16, for this second embodiment, the following steps are further added to the flowchart of the first embodiment. Firstly, make the ultrasonic probe 6 perform a predetermined initial operation in a state thereof the skin 8 of the human cheek as the target object to be measured is placed in contact with the upper surface of the resin plate 9. Then, make the CPU31 sequentially execute the processing by the above steps S100 to S160, thus showing on the display device 36 the acoustic-impedance images (tomographic images) that are color-coded according to the magnitude of the acoustic impedance of the cheek skin 8.

Subsequently, the CPU31 executes a thickness-calculation step for calculating the thickness of at least one of the layers that constitute the skin 8 based on the obtained acoustic-impedance distribution in the depth direction (step S170). The second embodiment of this invention calculates the average thickness of the papillary layer 66, more specifically the average thickness of the papillary layer 66 (and/or the thickness variation of the papillary layer 66) by extracting a portion thereof the acoustic impedance that is lower than that of the surrounding tissue in the depth direction of the skin 8 with the definition that such a portion is the papillary layer 66. Then, the CPU31 evaluates the state of the skin 8 of the cheek (specifically, aging degree/health degree) based on the average thickness of the papillary layer 66 calculated in the thickness-calculating step to prepare the evaluation-result-image data based on this evaluation, thus displaying then such image data on the display device 36 (step S180). After displaying the evaluation result, the CPU31 ends the series of processes. Also, the evaluation result may be displayed, for example, as a graph in which a plurality of average thicknesses are plotted, or only as a sentence or an icon.

According to the ultrasonic skin-condition-evaluation apparatus 1 as the second embodiment configured as described above, the apparatus itself can evaluate the condition of the skin 8 automatically and accurately, even if a person does not finally make a visual observation with the naked eye.

Third Embodiment

Hereinafter, an ultrasonic skin-condition-evaluation apparatus 101 as the third embodiment that embodies the ultrasonic-image-construction method and its apparatus of this invention will be described in detail with reference to FIGS. 17 and 18. Also, regarding the structure that is common with the structure of the aforementioned first embodiment, detailed description is omitted instead of indicating the reference numbers of the same member.

Figure 17:
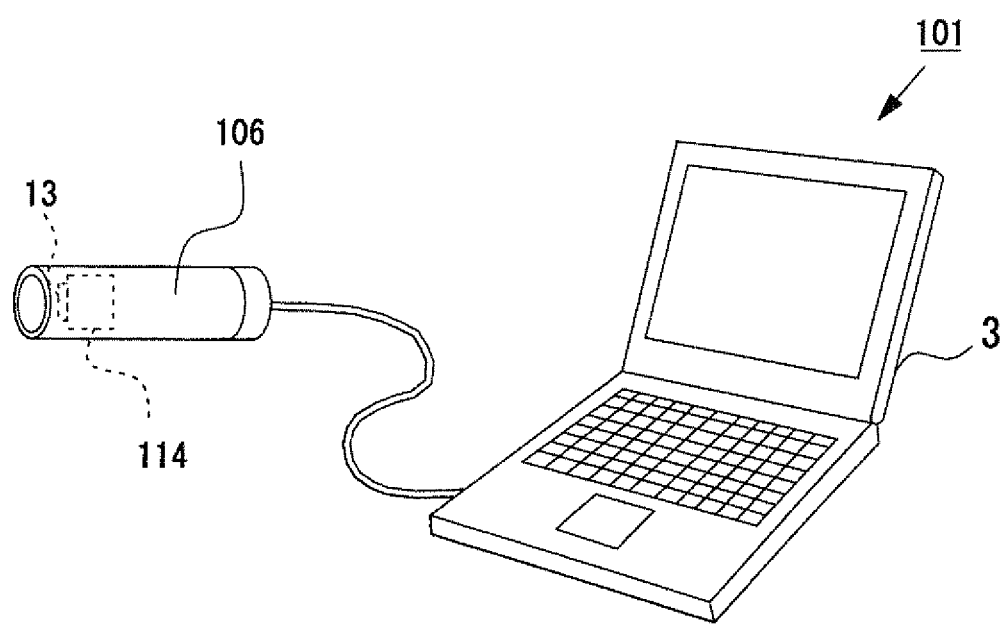
FIG. 17 is a schematic diagram showing the ultrasonic skin-condition-evaluation apparatus as the third embodiment of this invention.
Figure 18:
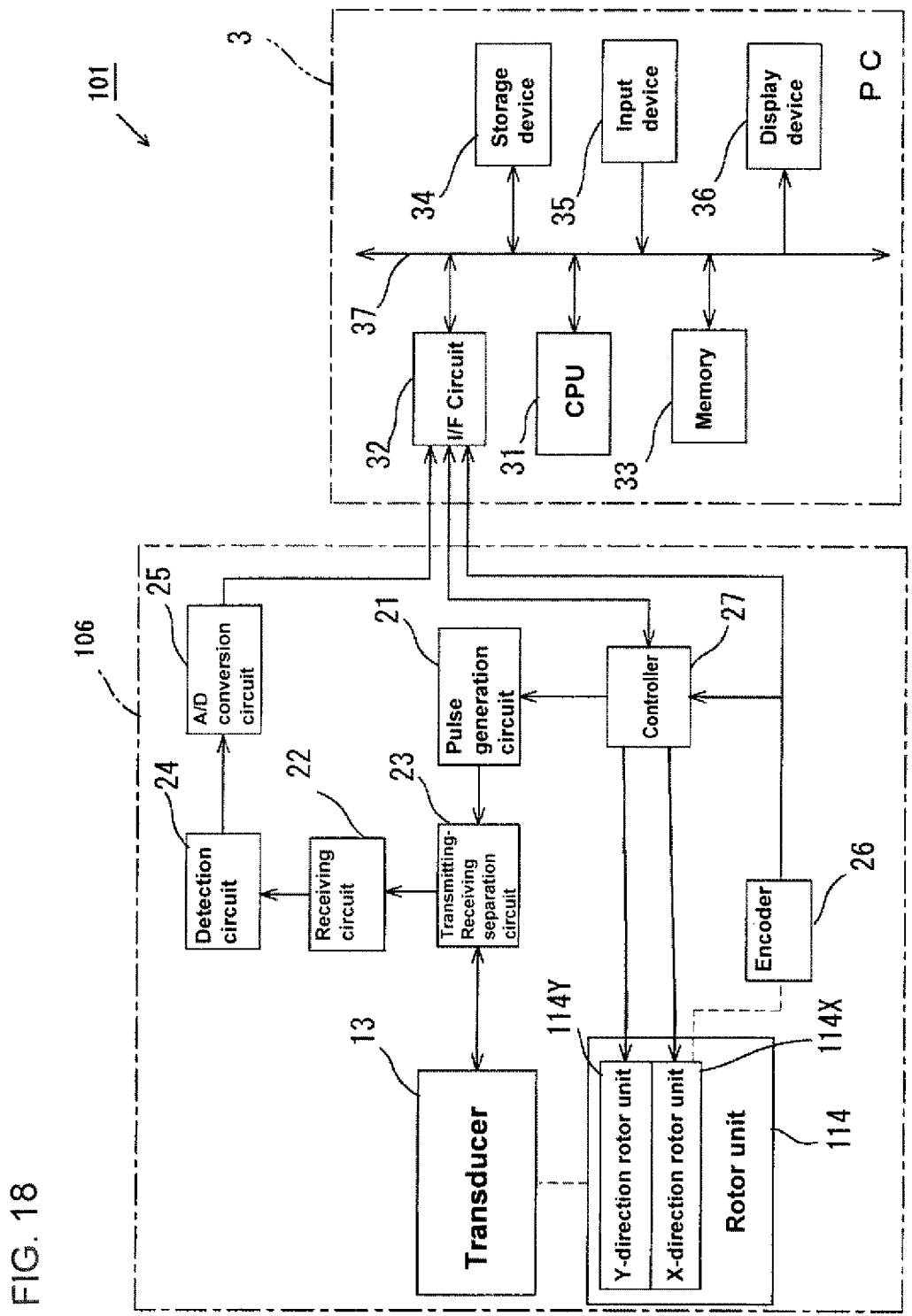
FIG. 18 is a block diagram showing the electrical constitution of the ultrasonic skin-state-evaluation apparatus as the third embodiment of this invention.

As shown in FIGS. 17 and 18, the ultrasonic skin-condition-evaluation apparatus 101 as the third embodiment of this invention comprises a gripping-probe device 106 of a shape and a size that enables an operator to hold and use such device by hand instead using the pulse-excitation-type ultrasonic microscope 2 that must be installed and used on a table or the like. The gripping-probe device 106 does not include the X-Y stage 14 or the motors 28X and 28Y but instead includes a rotor unit 114 consisting of an X-direction-rotor portion 114X and a Y-direction-rotor portion 114Y as a scanning means. By driving the rotor unit 114, the ultrasonic irradiation point is two-dimensionally scanned.

The aforementioned embodiments can be modified as described below.

In the ultrasonic skin-condition-evaluation apparatuses 1 and 101 as described above, the calculation process is performed using the reflected wave from the reference member 10 as a reference waveform. However, it is not limited to this. The reference waveform may be a reflected wave from a location where the skin 8 is not in contact with the upper surface of the resin plate 9. The reflected wave, for example, on a location where the skin 8 and the reference member 10 are not in contact with the upper surface of the resin plate 9 (Specifically, the reflected wave on the surface of the resin plate positioned outside the reference member 10) can also be used.

In the ultrasonic skin-condition-evaluation apparatuses 1 and 101 of the above embodiment, ultrasonic irradiation is done using the inverted ultrasonic microscope 2 that irradiates ultrasonic waves from below, but the upright ultrasonic microscope that irradiates ultrasonic waves from above can also be used.

In the above embodiment, the ultrasonic skin-condition-evaluation apparatuses 1 and 101 are used for the purpose of evaluating the condition of the relatively healthy skin 8 that basically has no disease, but the purpose is not limited to this. For example, the ultrasonic skin-condition-evaluation apparatuses 1 and 101 can also be used for the purpose of detecting the early stage of skin abnormalities associated with diseases such as skin cancer or the like.

In the ultrasonic skin-condition-evaluation apparatuses 1 and 101 of the above-described embodiment, the target object to be measured is human-cheek skin 8, but it may of course be the skin 8 of something other than the cheek. Also, the target object to be measured for the ultrasonic image-construction apparatuses 1 and 101 of this invention may not be the skin 8 but may be an internal organ, a muscle, a brain, a tooth, a nail, a bone-surface layer or the like. Furthermore, the target object to be measured may not necessarily be a biological tissue (organism) but may be a non-organism (for example, a coat film, or the like). In other words, the ultrasonic-image-constructing apparatuses 1 and 101 of this invention are not limited to be used in just the medical field, or the beauty field or the cosmetic field but can be used in other fields such as the industrial field or the like.

Although the ultrasonic skin-condition-evaluation apparatuses 1 and 101 of the above embodiments comprise a scanning means to make the ultrasonic transducer 13 relatively scan a target object to be measured in a two-dimensional direction, instead of just this use, such an apparatus can also comprise a scanning means to make the ultrasonic transducer 13 relatively scan only in a one-dimensional direction. Further, since the scanning means is not an essential configuration, it may of course be omitted. In this case, the apparatus can be reduced in size, simplified and reduced in cost.

In the ultrasonic skin-condition-evaluation apparatus 101 as the above third embodiment, the gripping-probe device 106 and the PC 3 are separated from each other, and the acoustic-impedance image is displayed on the display device 36 of the PC 3, but this invention is not limited to this. For example, a small display device 36 may be provided in the gripping-probe device 106, thus displaying an acoustic-impedance image on the small display device 36. Furthermore, the gripping-probe device 106 itself may have an integrated configuration in which the function of the PC 3 is incorporated, thus displaying the acoustic-impedance image on the small display device 36 provided in the gripping-probe device 106.

In the ultrasonic skin-condition-evaluation apparatuses 1 and 101 of the above-described embodiments, the acoustic-impedance image is constructed based on the estimated result of the acoustic-impedance distribution in the depth direction, but this invention is not limited to this. For example, the sound-velocity distribution in the depth direction may be estimated, and based on the result a sound-velocity image can be constructed.

In the ultrasonic skin-condition-evaluation apparatuses 1 and 101 of the above embodiments, the acoustic-impedance image is constructed from the reflected-signal sequence that is the basis of the ultrasonic B-mode echo image and is displayed on the display device 36. However, it is of course possible to make not only the acoustic-impedance image but the ultrasonic B-mode echo image displayed on the display device 36. Further, it is possible to incorporate the conversion algorithm of the above-described embodiment into a general-purpose ultrasonic-diagnostic apparatus that displays an ultrasonic B-mode echo image, thus operating the ultrasonic skin-condition-evaluation apparatus.

The above-described embodiment employs a technique of converting a reflected-signal sequence that is the base of an ultrasonic B-mode echo image into an acoustic-impedance image in the depth direction through analysis in the time-frequency domain in consideration of the multiple reflections inside the skin tissue. However, it is not limited to this. As a method for estimating the distribution of characteristic impedance from the reflected waveform, it is also possible to adopt, for example, a method for accordingly analyzing the response on the time axis, assuming that all of the reflection paths, including multiple reflections, are inside the transmission path. Even by this method, it is possible to obtain the same estimated result of the characteristic impedance distribution as that by the method of the above embodiment.

DESCRIPTION OF THE REFERENCE NUMERALS 1, 101: Ultrasonic skin condition evaluation apparatus as an ultrasonic image construction apparatus
8: Biological tissue (skin) as a target object to be measured
9: Resin plate as a base substrate
10: Reference member as a reference substance
13: Ultrasonic transducer
14: X-Y stage as a scanning means
31: Computing means, Image construction means, CPU as a processor
51: Micro-transmission path
66: Papillary layer
114: Rotor unit as a scanning means
$\Gamma_0, \Gamma_1$: Impulse response

The invention claimed is:

1. An ultrasonic-image-construction method, comprising;
a transmitting-and-receiving step for transmitting ultrasonic waves at a biological tissue having a layered structure and a reference substance, wherein the biological tissue to be measured and the reference substance of known acoustic properties are in contact with a base substrate of known acoustic properties, and then receiving impulse responses of the ultrasonic waves from the biological tissue to be measured and from the reference substance, with such ultrasonic waves being incident on the biological tissue to be measured and on the reference substance through the base substrate;
a computing step for performing a calculation to estimate an acoustic impedance distribution in a depth direction of micro-transmission paths in consideration of an effect of multiple reflections based on normalized impulse-response information having been obtained from impulse-response information of the ultrasonic waves incident on the reference substance and of impulse-response information of the ultrasonic waves incident on the biological tissue to be measured;
the computing step further comprising:
i) assuming micro-transmission paths of different acoustic impedances are connected in the depth direction to form an assembly of micro-transmission paths;
ii) estimating an acoustic impedance of the micro-transmission path on a front side; and
iii) estimating an acoustic impedance of the micro-transmission path adjacent to a back side by using the estimate of the acoustic impedance of the micro-transmission path on the front side;
steps (i-iii) form part of the calculation to estimate the acoustic impedance distribution; and
in comprising an image-construction step for constructing an acoustic-property image data based on the acoustic impedance distribution in the depth direction obtained by a computer.

2. An ultrasonic image-construction method according to claim 1, characterized in that the biological tissue to be measured is skin.

3. An ultrasonic-image-construction method according claim 1, characterized in that the base substrate is at least partially flat and is made of a material harder than the biological tissue to be measured.

4. An ultrasonic-image-construction method according to claim 1, characterized in that the reference substance of known acoustic properties that is different from the base substrate is already provided on the surface of the base substrate on which the biological tissue to be measured is arranged.

5. An ultrasonic-image-construction method according to claim 1, characterized in that in the transmitting-receiving step an ultrasonic wave is incident on the biological tissue to be measured while such ultrasonic wave is relatively scanning in a one-dimensional or two-dimensional direction.

6. An ultrasonic-image-construction apparatus, comprising:
an ultrasonic transducer that transmits ultrasonic waves at a biological tissue having a layered structure and a reference substance, wherein the biological tissue to be measured and the reference substance of known acoustic properties are in contact with a base substrate of known acoustic properties, the ultrasonic transducer also receives impulse responses of the ultrasonic waves from the biological tissue to be measured and from the reference substance, with the ultrasonic waves being incident on the biological tissue to be measured and on the reference substance through the base substrate,
a computer for estimating an acoustic impedance distribution in a depth direction of micro-transmission paths path in consideration of an effect of multiple reflections based on impulse-response information of the ultrasonic waves having been incident on the reference substance and based on normalized impulse-response information having been obtained from the impulse-response information of the ultrasonic waves having been incident on the biological tissue to be measured, and
the computer further;
i) assuming micro-transmission paths of different acoustic impedances are connected in the depth direction to form an assembly of micro-transmission paths;
ii) estimating an acoustic impedance of the micro-transmission path on a front side; and
iii) estimating an acoustic impedance of the micro-transmission path adjacent to a back side by using the estimate of the acoustic impedance of the micro-transmission path on the front side;

steps (i-iii) form part of the estimate of the acoustic impedance distribution performed by the computer;

the computer configured for constructing an acoustic-property image data based on the acoustic-impedance distribution in the depth direction obtained by the computer.

7. An ultrasonic-image-construction apparatus according to claim 6, characterized in further comprising a scanner for relatively scanning the ultrasonic transducer to the biological tissue to be measured in a one-dimensional or two-dimensional direction.

8. An ultrasonic-image-construction program to run a processor;

to execute a transmitting-and-receiving step for transmitting ultrasonic waves at a biological tissue having a layered structure and a reference substance, wherein the biological tissue to be measured and a reference substance of known acoustic properties are in contact with a base substrate of known acoustic properties, and then for receiving impulse responses of the ultrasonic waves from the biological tissue to be measured and from the reference substance, with such ultrasonic waves being incident on the biological tissue to be measured and on the reference substance through the base substrate;

to execute a calculating step for performing a calculation to estimate an acoustic impedance distribution in a depth direction of micro-transmission paths in consideration of an effect of multiple reflections based on normalized impulse-response information having been obtained from impulse-response information of the ultrasonic waves incident on the reference substance and of impulse-response information of the ultrasonic waveform incident on the biological tissue to be measured;

the executing of the calculating step further comprising:

i) assuming micro-transmission paths of different acoustic impedances are connected in the depth direction to form an assembly of micro-transmission paths;

ii) estimating an acoustic impedance of the micro-transmission path on a front side; and iii) estimating an acoustic impedance of the micro-transmission path adjacent to a back side by using the estimate of the acoustic impedance of the micro-transmission path on the front side;

steps (i-iii) form part of the calculation to estimate the acoustic impedance distribution;

and to execute an image construction step for constructing an acoustic-property image data based on the acoustic-impedance distribution in the depth direction.

9. A cosmetic skin-evaluation method, characterized in comprising:

a transmitting-and-receiving step for transmitting ultrasonic waves at a biological tissue having a layered structure and a reference substance, wherein the biological tissue to be measured and the reference substance of known acoustic properties are placed in contact with a base substrate of known acoustic properties, and then for receiving impulse responses of the ultrasonic waves from the biological tissue to be measured and from the reference substance, with the ultrasonic waves having been incident on the biological tissue to be measured and on the reference substance through the base substrate;

a computing step for estimating an acoustic property distribution in a depth direction of micro-transmission paths in consideration of an effect of the multiple reflections based on impulse-response information of the ultrasonic waves having been incident on the reference substance and based on normalized impulse-response information having been obtained from impulse-response information of the ultrasonic waves having been incident on the biological tissue to be measured, the computing step further comprising:

i) assuming micro-transmission paths of different acoustic impedances are connected in the depth direction to form an assembly of micro-transmission paths;

ii) estimating an acoustic impedance of the micro-transmission path on a front side; and iii) estimating an acoustic impedance of the micro-transmission path adjacent to a back side by using the estimate of the acoustic impedance of the micro-transmission path on the front side;

steps (i-iii) form part of the calculation to estimate the acoustic impedance distribution;

a calculation step for calculating a thickness of at least one of the layers that constitute the skin based on the obtained acoustic-impedance distribution in the depth direction;

and an evaluation step for evaluating a skin condition based on the thickness of the layer obtained in the calculation step.

10. A cosmetic skin-evaluation method according to claim 9, characterized in that in the calculation step the thickness of the papillary layer constituting the skin is calculated based on the obtained acoustic impedance distribution in the depth direction.

11. A cosmetic skin-evaluation method according to claim 9, characterized in further comprising an image-construction step for constructing image data of an acoustic-property image based on the obtained acoustic impedance distribution in the depth direction.

* * * * *